United States Patent [19]

Mulder et al.

[11] 4,218,348
[45] Aug. 19, 1980

[54] ESTERS OF 1,5-DIMETHYLBICYCLO-[3,2,1]OCTAN-8-OL

[75] Inventors: Albertus J. Mulder; Aaldert J. de Jong, both of Amsterdam, Netherlands

[73] Assignee: Shell Oil Company, Houston, Tex.

[21] Appl. No.: 37,196

[22] Filed: May 8, 1979

[30] Foreign Application Priority Data

May 12, 1978 [NL] Netherlands ............... 7805143

[51] Int. Cl.² ............... A61K 7/46; C07C 101/52
[52] U.S. Cl. ............... 252/522R; 260/410; 560/1; 560/19; 560/107; 560/121; 560/123; 560/124; 560/256; 560/220; 252/522 A
[58] Field of Search ............... 560/1,256,107,19, 121, 560/123, 124; 560/220; 252/522; 260/410 R

[56] References Cited

U.S. PATENT DOCUMENTS

| | | | |
|---|---|---|---|
| 3,417,132 | 12/1968 | Duakel | 560/256 |
| 3,681,464 | 8/1972 | Theimer | 560/256 X |

OTHER PUBLICATIONS

Mason et al., J.A.C.S., 95(6), 1849, (1973).

Tabushi et al., J. Organic Chem., 35(7), 2376–2382, (1970).
Harding et al., J. Org. Chem., vol. 40, No. 7, pp. 929–935, (1975).
Mason et al., J.A.C.S., 95:6, pp. 1849–1859, (1973).
Gove, Webster's Third New International Dictionary, G. & C. Merrian Co., Springfield, Mass. p. 53, 1963.

*Primary Examiner*—G. T. Breitenstein

[57] ABSTRACT

Esters of 1,5-dimethylbicyclo[3,2,1]octan-8-ol of the general formula:

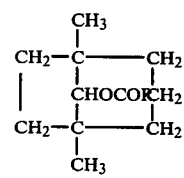

wherein R represents hydrogen or an aliphatic or an aromatic hydrocarbon group optionally substituted with an amino group; are useful as aroma chemicals.

7 Claims, No Drawings

ESTERS OF 1,5-DIMETHYLBICYCLO-[3,2,1]OCTAN-8-OL

BACKGROUND OF THE INVENTION

This invention relates to a novel class of 1,5-dimethylbicyclo[3,2,1]octane derivatives which are of interest as aroma chemicals. More particularly, this invention is directed to novel esters of 1,5-dimethylbicyclo[3,2,1]octan-8-ol, their use as perfume compounds and perfume compositions containing them.

A variety of hydroxy- and carbonyl-substituted organic compounds (including esters) are known in the art to possess aroma properties which are useful in the perfumery field. In the past, many of these organic compounds have been derived from naturally occurring substances (terpenes and terpene derivatives). More recently, there has been a growing interest in the preparation and use of synthetic perfume materials. This interest is stimulated not only by the lack of an adequate supply of natural products, but also by the fact that, unlike natural products, synthetic perfumes can be produced with constant quality.

1,5-Dimethylbicyclo[3,2,1]octan-8-ol is known compound, its preparation by reaction of 1,5-dimethyl-1,5-cyclooctadiene with perchloric acid in a water-dioxane solution having been described previously in an article by J. K. Whitesell et al in Tetrahedron Letters No. 19, pp. 1549–1552 (1976). However, carboxylic acid esters of this bicyclic alcohol and the distinctive aroma properties of such esters have not heretofore been disclosed.

SUMMARY OF THE INVENTION

A novel class of carboxylic acid esters of 1,5-dimethylbicyclo-[3,2,1]octan-8-ol have now been found which are valuable perfume compounds with a strong flowery and/or minty odor with a pleasant woody note. This novel class of 1,5-dimethylbicyclo[3,2,1]octan-8-ol esters is represented by the general formula:

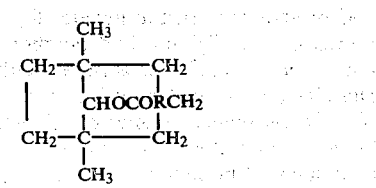

wherein R represents hydrogen, a saturated or unsaturated aliphatic group of 1 to 10 carbon atoms or an aromatic hydrocarbon group of up to 7 carbon atoms, optionally substituted with an amino group. The compounds of the invention comprises both compounds with the syn and with the anti configuration.

DESCRIPTION OF THE PREFERRED EMBODIMENTS

Preferred esters of the general formula above are those in which R is hydrogen, an aliphatic hydrocarbon of 1 to 7 carbon atoms which may be saturated or unsaturated and branched, unbranched or cyclic or an aromatic hydrocarbon group of 6 carbon atoms optionally substituted with an amino group. Suitable aliphatic hydrocarbon substituents in the general formula above include alkyl, alkenyl, alkynyl and cycloalkyl groups. Suitable aromatic hydrocarbon substituents are phenyl and ortho-, meta-, or para-aminophenyl. Particularly preferred esters are those wherein R in the general formula above is hydrogen or an aliphatic hydrocarbon group of from 1 to 4 carbon atoms.

Examples of compounds according to the invention falling under the general formula above are the formate, acetate, propionate, butyrate, isobutyrate, pivalate, valerate and anthranilate of 1,5-dimethylbicyclo-[3,2,1]octan-8-ol.

The compounds according to the invention may be used as such as fragrance materials but they can also successfully be used in perfume compositions.

The term "perfume composition" as used herein means a mixture comprising fragrance and, optionally, auxiliary components, dissolved in a suitable solvent or mixed with a powdery substrate if desired, and used to impart a desirable odor to the skin and/or to various kinds of products.

Examples of such products are: soaps, detergents, dishwashing and cleansing agents, air fresheners and room deodorants, pomanders, candles, cosmetics such as creams, ointments, toilet waters, pre- and aftershave lotions, talcum powders, hair care products, body deodorants and antiperspirants.

Fragrance components and mixtures thereof which can be used in preparing perfume compositions may include natural products like essential oils, absolutes, resinoids, balsems and concretes, but also synthetic fragrance compounds such as e.g. hydrocarbons, alcohols, aldehydes, ketones, ethers, acids, esters, acetals, ketals, and nitriles, which may be saturated or unsaturated aliphatic, carbocyclic or heterocyclic compounds.

Examples of fragrance compounds which can be used in combination with compounds according to the invention are: geraniol, geranyl acetate, linalool, linalyl acetate, tetrahydro linalool, citronellol citronellyl acetate, myrcenol, myrcenyl acetate, dihydromyrcenol, terpineol, terpinyl acetate, nopol, nopyl acetate, beta-phenylethanol, betaphenylethyl acetate, benzyl alcohol, benzyl acetate, benzyl salicylate, benzyl benzoate, amyl salicylate, styrallyl acetate, dimethylbenzyl carbinol, trichloromethyl-phenyl-carbonyl acetate, p-tert,butylcyclohexyl acetate, iso-nonyl acetate, vetiveryl acetate, vetiverol, alpha-hexyl cinnamaldehyde, alpha-n-pentyl cinnamaldehyde, 2-methyl-3-(p-tert.butylphenyl)-propanal, 2-methyl-3(p-iso-propylphenyl)-propanol, 3-(p-tert.butylphenyl)-propanol, tricyclododecenyl acetate, tricyclododecenyl propionate, 4-(4-hydroxy-4-methyl pentyl)-3-cyclohexene carbaldehyde, 4-(4-methyl-3-pentenyl)-3-cyclohexene carbaldehyde, 4-acetoxy-3-pentyltetrahydropyran, 3-carboxymethyl-2-pentylcyclopentane, 2-n-heptylcyhopentanone, 3-methyl-2-pentyl-2-cyclopentanone, 2-hexyl-2-cyclopentanone, n-decanal, n-dodecanal, 9-decenol-1, phenoxyethyl isobutyrate, phenylacetaldehyde dimethyl acetal, phenylacetaldehyde diethylacetal, geranyl nitrile, citronellyl nitrile, cedryl acetate, 3-iso-camphyl-cyclohexanol, cedryl methyl ether, isolongifolanone, aubepine nitrile, heliotropine, coumarin, eugenol, vanilbin, diphenyl oxide, hydroxycitronellal, ionones, methyl ionones, iso-methyl ionones, irones, cis-3-hexenol and ester thereof, indan-musk fragrances, tetralin musk fragrances, isochroman musk fragrances, macrocyclic ketones, macrolacton musk fragrances, ethylene brassilate, aromatic nitro musk fragrances.

Auxiliary components and solvents which may be used for the preparation of perfume compositions containing compounds according to the invention are, e.g., ethanol, isopropanol, diethylene-glycol monoethyl ether and diethyl phthalate.

The amount of the derivative of 1,5-dimethylbicyclo[3,2,1]octane with the general formula above that can be used in a perfume composition or in a product to be perfumed may vary within wide limits and depends, among other factors, on the product to be perfumed, the nature and the amount of the other components of the perfume composition and the overall odor effect sought to be achieved. Therefore, it is only possible to state very rough limits, which will, however, give the expert an idea of the odor strength and the potentialities of the fragrance compounds according to the invention. In most cases an amount as low as 0.01% by weight will be sufficient to impart a slight, but clearly perceptible flowery or minty note to a perfume composition or to a product to be perfumed. In so-called extract perfumes and in products perfumed with perfume compositions this concentration is, of course, proportionally lower, depending on the amount of perfume composition used in the end product.

The compounds with the general formula above are esters which can be synthesized by various methods known for the preparation of esters. 1,5-Dimethylbicyclo[3,2,1]octan-8-ol may, for example, be reacted with a carboxylic acid RCOOH, wherein R has the above-mentioned meaning, optionally in the presence of a catalyst such as, for instance, sulfuric acid, hydrogen chloride, boron trifluoride or an acid ion exchange resin. Or 1,5-dimethylbicyclo[3,2,1]octan-8-ol may be reacted with the acid chloride of the desired carboxylic acid in the presence of a catalyst such as e.g. sodium acetate, pyridine or trimethylamine or with the acid anhydride of the carboxylic acid, optionally in the presence of a catalyst such as sulfuric acid, boron trifluoride or an acid ion exchange resin.

In many cases the ester can be obtained in high yield by heating 1,5-dimethylbicyclo[3,2,1]octan-8-ol with a mixture of a carboxylic acid, such as for example acetic acid, propionic acid, butyric acid, isobutyric acid, valeric acid or pivalic acid and the anhydride of the carboxylic acid concerned, preferably at a temperature between 100° and 180° C. in the presence of an acidic ion exchange resin, such as for instance the strongly acid macroreticular cation exchange resin "AMBERLYST" 15, It is preferred to use a small excess of the carboxylic acid anhydride, such as 5% m calculated on 1,5-dimethylbicyclo[3,2,1]octan-8-ol. The compound with the general formula above, wherein R is hydrogen, the formate, may be obtained in high yield by heating 1,5-dimethylbicyclo-[3,2,1]octan-8-ol with formic acid.

As mentioned previously, 1,5-dimethylbicyclo[3,2,-1]octan-8-ol and its preparation by reaction of 1,5-dimethyl-1,5-cyclooctadiene with a solution of HClO$_4$ in water-dioxane has been described in an article by J. K. Whitesell, R. S. Matthews and P. A. Solomon in Tetrahedron Letters No. 19, pp. 1549–1552 (1976). With this method the yield of the desired product is only 50%. In addition, the use of perchloric acid has disadvantages. However, the compound can be otained in higher yield by hydrolysis or alcoholysis, for instance with sodium methylate in methanol, of the formate of 1,5-dimethylbicyclo[3,2,1)octan-8-ol which can be prepared in very high yield by means of a new process from 1,5-dimethyl-1,5-cyclooctadiene. This new process is the subject of our copending U.S. patent application Ser. No. 37,195 filed May 8, 1979.

According to the new process compounds with the general formula I can be prepared by reacting 1,5-dimethyl-1,5-cyclooctadiene, optionally in the presence of an acidic catalyst, with carboxylic acid with the formula RCOOH, wherein R has the above-mentioned meaning. This process is particularly suitable for the preparation of the formate of 1,5-dimethylbicyclo[3,2,-1]octan-8-ol which can be obtained in high yield by heating 1,5-dimethyl-1,5-cyclooctadiene with formic acid, preferably at a temperature between 40° and 100° C. It is preferred to use an excess of formic acid, for instance 2 to 10 moles per mole of the dimethylcyclooctadiene. Addition of a catalyst is not necessary. The excess of formic acid may be distilled off after the reaction and the residue be worked up using conventional procedures, for instance by diluting with a solvent, neutral washing and fractional distillation. Although it it preferred to use formic acid with a water content of from 0 to 10% w, it is possible, if desired, to use formic acid with a higher water content of from 10 to 40% w, in particular when a phase transfer catalyst, such as for example tri-sec. octyl-methyl-ammonium chloride ("ALIQUAT"), is added to the reaction mixture.

When this new process is employed to react 1,5-dimethyl-1,5-cyclooctadiene with the carboxylic acid RCOOH, having a pKa value greater than 4, the addition of an acid catalyst to the reaction mixture is generally necessary for satisfactory reaction rates and conversions. Suitable catalysts are e.g. sulfuric acid, phosphoric acid, p-toluene sulfonic acid and in particular acid cation exchange resins, such as for instance "AMBERLYST" 15.

In the new process, a suitable starting material is a mixture consisting of 1,5- and 1,6-dimethyl-1,5-cyclooctadiene, which, as is mentioned in French Pat. No. 1,283,217 can be obtained by dimerization of isoprene. The presence of 1,6-dimethyl-1,5-cyclooctadiene in the reaction mixture does not interfere with the formation of the desired ester and its separation from the reaction mixture.

Compounds with the general formula I, wherein R represents an aliphatic hydrocarbon group or an aromatic one optionally substituted with an amino group, can also be obtained by using transesterification methods. For instance, an ester of 1,5-dimethylbicyclo[3,2,-1]octan-8-ol and a lower carboxylic acid RCOOH can be converted into an ester of the said compound and a higher carboxylic acid RCOOH. For example, transesterification of the format of 1,5-dimethylbicyclo[3,2,-1]octan-8-ol may be effected with an ester RCOOR$_1$, wherein R represents a primary or secondary alkyl group with preferably from 1 to 7 carbon atoms and R$_1$ a primary alkyl group with preferably from 1 to 3 carbon atoms, in particular a methyl or an ethyl group. The esters, for example the anthranilate of 1,5-dimethylbicyclo[3,2,1]octan-8-ol, can also be obtained by transesterification of 1,5-dimethylbicyclo[3,2,1]octan-8-ol with an ester of the desired acid and a primary alcohol with from 1 to 4 carbon atoms, for instance methyl anthranilate, in the presence of a catalyst.

A very convenient catalyst for the transesterification is an alkali or alkaline-earth metal alcoholate of 1,5-dimethylbicyclo[3,2,1]-octan-8-ol. The amount of catalyst employed is preferably between 1 and 10, in particular between 2 and 6% m, calculated on the starting ester of 1,5-dimethylbicyclo[3,2,1]octan-8-ol. If desired, the alcoholate may be prepared in situ from the alkali or alkaline-earth metal, e.g. sodium and 1,5-dimethylbicyclo[3,2,1]octan-8-ol, by adding these components to the transesterification mixture. On the other hand, the alcoholate may be prepared separately, for instance by heating the alkali metal or the hydride thereof under nitrogen with an excess of 1,5-dimethylbicyclo[3,2,1]octan-8-ol at 60°-200° C. and then distilling off the excess of the later compound.

EXAMPLE I

Preparation of the formate of 1,5-dimethylbicyclo[3,2,1]octan-8-ol

An amount of 420 ml (11.46 mol) 98-100% formic acid was introduced into a round-bottom flask and with vigorous stirring 430 ml (2.74 mol) dimethyl-1,5-cyclooctadiene (a mixture of 80% w 1,5-dimethyl-1,5-cyclooctadiene and 20% w 1,6-dimethyl-1,5-cyclooctadiene) was added to the formic acid at a temperature of 60° C. over a period of 1.5 hours. At the end of the addition period, the dimethylcyclooctadiene was completely converted. Subsequently, 90% of the formic acid was distilled off in vacuo at 60° C. together with a bicyclic olefin, which was isolated by means of extraction with pentane. The residue was taken up in 200 ml pentane and washed with water and an aqueous solution of NaHCO$_3$. After drying over Na$_2$SO$_4$ the pentane was distilled off and the residue fractionally distilled in vacuo. The yield of the formate of 1,5-dimethylbicyclo[3,2,1]octan-8-ol boiling point 69° C. at 133 Pa (pascal), was 392 g (2.15 mol; 97%, calculated on 1,5-dimethyl-1,5-cyclooctadiene). By means of gas chromatography the purity was shown to be higher than 99%. The product was indentified by measuring the infrared- and NMR-spectra. Infrared spectrum: 1000, 1185 and 1730 cm$^{-1}$. The formate consisted of 92% w syn and 8% anti isomer. Repetition of the experiment with formic acid which contained 10% w water produced the formate in a yield of 94.8%, calculated on 1,5-dimethyl-1,5-cyclooctadiene. When formic acid with a higher water content (40% w) was used, addition of a phase transfer catalyst was found to be necessary to obtain reasonable yields.

The formate of 1,5-dimethylbicyclo[3,2,1]octan-8-ol has a fresh, minty odor with a slight woddy note.

EXAMPLE II preparation of the acetate of 1,5-dimethylbicyclo[3,2,1]octan-8-ol (1) An amount of 182 g of the formate of 1,5-dimethylbicyclo[3,2,1]-octan-8-ol was dissolved in 100 ml methanol and the solution was slowly added to a mixture of 50 g NaOH, 50 ml H$_2$O and 200 ml methanol. After the exothermic reaction had come to and end, boiling was continued for 10 minutes under reflux. The methanol was distilled off in vacue and pentane was added to the residue. After washing with water and drying over Na$_2$SO$_4$, 152 g crystalline 1,5-dimethylbicyclo[3,2,1]octan-8-ol was obtained (melting point 43° C.) by concentrating and cooling of the pentane solution. The yield was quantitative. The structure was confirmed by measuring the infrared- and NMR-spectra. The weights of synand anti-isomer were in the ratio of 92:8.

(2) 1,5-Dimethylbicyclo[3,2,1]octan-8-ol was also prepared by dissolving 8.8 g of the formate of 1,5-dimethylbicyclo[3,2,1]octan-8-ol in 50 ml absolute methanol and adding 10 mg of sodium to the solution. After refluxing for four hours, methanol and formed methyl formate were distilled off and the residue was taken up in pentane. The solution was washed with water and dried over Na$_2$SO$_4$. Distilling off the pentane yielded 6 g crystalline product with a purity higher than 98%.

(b) Acetylation of 1,5-dimethylbicyclo[3,2,1]octan-8-ol

An amount of 20g (0.13 mol) 1,5-dimethylbicyclo[3,2,1]octan-8-ol was dissolved in 25ml acetic acid and 15 g (0.14 mol) acetic anydride and 0.2 g "AMBERLYST" 15 ion exchange resin were added to the solution. After being heated for 5 minutes at 100° C. the reaction mixture was filtered and acetic acid and acetic anhydride were distilled off. The residue was dissolved in pentane and the solution washed with water and NaHCO$_3$ solution. After being dried over Na$_2$SO$_4$ the pentane was distilled off and the residue fractionally distilled vacuo. By this procedure, 25 g of the acetate of 1,5-dimethylbicyclo-[3,2,1]octan-8-ol was obtained with a boiling point of 74° C. at a pressure of 80 Pa. Infrared spectrum: 1050; 1235 and 1740 cm$^{-1}$. The weights of the syn and anti isomer were in the ratio of 92:8. the acetate has a fresh, flowery odor with a woody note.

EXAMPLE III

Preparation of the acetate of 1,5-diemthylbicyclo[3,2,1]octan-8-ol by transesterification of the formate.

An amount of 20 g (0.11 mol) of the formate of 1,5-dimethylbicyclo[3,2,1]octan-8-ol was dissolved in 60 ml ethyl acetate, and 130 gm Na and 850 mg 1,5-dimethylbicyclo[3,2,1]octan-8-ol were added to the solution. The mixture was refluxed for 3 hours resulting in complete dissolution of the sodium. It has shown by gas chromatography that 38% of the formate had been converted into the acetate. The flask was now fitted with a Vigreux distillation column and a mixture of ethyl formate and ethyl acetate was distilled off over a period of 3.5 hours at a temperature of 60° C. During the distillation 30 ml ethyl acetate was added. At the end of the distillation it was shown by gas chromatography that more than 95% of the formate had been converted. Subsequently, 50 ml of pentane was added and the precipitated sodium alcohol of 1,5-dimethylbicyclo[3,2,1]octan-8-ol filtered off. The filtrate was washed with water and dried over Na$_2$SO$_4$. After the pentane had been distilled off, the residue was fractionally distilled in vacuo to afford 21 g of the desired acetate with a boiling point of 74° C. at a pressure of 80 Pa. The yield was 97.4% calculated on the formate. The 1,5-dimethylbicyclo-[3,2,1]octan-8ol added was quantitatively recovered in the form of the alcholate.

EXAMPLE IV

Preparation of the propionate, butyrate, isobutyrate, pivalate and valerate of 1,5-dimethylbicycl[3,2,1]-octan-8-ol These esters were prepared in an analogous way to that described for the acetate in Example IIb. 1,5-Dimethylbicyclo[3,2,1]-octan-8-ol was dissolved in a mixture of each carboxylic acid and the anhydride thereof. The catalyst was "AMBERLYST" 15, which was added in an amount of 1% w calculated on the amount of dimethylbicyclooctanol used. In all cases an excess of 5% m acid anhyride was used. The reaction mixture was heated at 120°-160° C. for 20 minutes. The carboxylic acid and the excess of anhydride were then substnatially removed by distillation in vacuo. The residue was taken up in pentane and the solution was washed with an 8% KOH solution in a mixture of 75%v water and 25%v methanol. Saponification of the esters formed did not occur during this procedure. After being dried over Na2SO4, the pentane was distilled in vacuo. The ester yield was always higher than 99%. Physical constants of the esters prepared using the above procedure are listed in the following table.

| Ester | Boiling Point | Melting Point | Infra-red Spectrum |
|---|---|---|---|
| Propionate | 86° C./40 Pa | | 1040; 1195; 1215; 1750 |
| Butyrate | 92° C./27 Pa | | 1030; 1180; 1215; 1740 |
| Isobutyrate | 88° C./27 Pa | | 1030; 1170; 1200; 1745 |
| Pivalate | 90° C./27 Pa | 61° C. | 1030; 1050; 1160; 1170; 1740 |
| Valerate | 99° C./27 Pa | | 1040; 1180; 1745 |

The propionate has a fresh, flowery odor with a strong woody note.

The pivalate has a fresh, minty odor with a woody note.

The butyrate has a fresh, flowery and woody odor.

The valerate has a fresh, minty odor with a woody note.

EXAMPLE V

Preparation of the acetate of 1,5-dimethylbicyclo[3,2,1]-octan-8-ol from dimethyl-1,5-cyclooctadiene (a) An amount of 20.4 g dimethyl-1,5-cyclooctadiene (a mixture of 80%W 1,5-dimethyl-1,5-cyclooctadiene and 20% w 1,6-dimethyl-1,5-cyclooctadiene) was dissolved in 100 ml acetic acid and, after addition of 2 g "AMBERLYST" 15, boiled under reflux with vigorous stirring. After six hours the conversion was 98%. The reaction mixture was filtered, diluted with water and extracted with pentane. The pentane solution was washed with water and an aqueous NaHCO3 solution, dried, evaporated and fractionally distilled. The yield of the desired acetate was 53.3%, calculated on 1,5-dimethyl-1.5-cyclooctadiene. The weight of the syn and anti isomer were in the ratio of 85:15.

(b) An amount of 13.6 g (0.1 mol) dimethyl-1,5-cyclooctadiene (a mixture of 80% w 1,5-dimethyl-1,5-cyclooctadiene and 20% w 1,6-dimethyl-1,5-cyclooctadiene) was dissolved in 60 ml acetic acid. The solution was cooled to 12° C. and 0.5 ml H2SO4 was added dropwise with vigorous stirring. During the addition the temperature increased to 39° C. After anothere two hours at room temperature the conversion of the dimethylcyclooctadiene was 98% and the reaction mixture was worked up in the way described under (a). The yield of the desired acetate was 24%, calculated on 1,5-dimethyl-1,5-cyclooctadiene. The weight of the syn and anti isomer were in the ratio of 85:15.

EXAMPLE VI

A mixture of 8 g of 1,5-dimethylbicyclo[3,2,1]-octan-8-ol, 8 g methyl anthranilate and 60 mg sodium heated at 140° C. for five hours, during which methanol was removed. The removal of the methanol was promoted by applying a slightly sub-stmospheric pressure. Then, water was added and the mixture obtained was extracted with cyclohexane. The extract was washed with 0.1 N H2SO4 to remove non-converted methyl anthranilate, and then with an aqueous NaHCO3 solution. After drying over Na2SO4, the cyclohexane was distilled off and the residue was fractionally distilled in vacuo to afford 9.5g of the anthranilate of 1,5-dimethylbicyclo[3,2,1] octan-8-ol with a boiling point of 117° C./40 Pa.

EXAMPLE VII a perfume composition for use in bath foam was prepared according to the recipe given below:
150 pbw terpineol
130 pbw phenylethanol
100 pbw benzyl salicylate
70 pbw 4,6,6,7,8,8-hexamethyl-6,7-dihydro-8H-cyclopental [g] isochroman
60 pbw alpha-hexyl cinnamic aldehyde
50 pbw 5-tert.butyl cyclohexyl acetate 50 pbw benzyl acetate
50 pbw linalool
40 pbw methyl ionone
pbw citronellol
40 pbw phenylethyl acetate
30 pbw geraniol
30 pbw lavender oil
20 pbw anisic aldehyde
10 cedryl acetate
10 pbw styallyl acetate
10 pbw benzoin resin Siam
10 pbw salbei oil
100 pbw 1,5-dimethylbicyclo [3,2,1 ] octan-8-yl formate
1000 pbw

EXAMPLE VIII

A perfume composition for use in toilet soap was prepared according to the recipe given below:
170 pbw lavender oil Jugoslave
100 pbw linalyl acetate
80 pbw bergamot oil
80 pbw dihydromyrcenol
70 pbw menthanyl acetate
50 pbw 4,6,6,7,8,8-hexamethyl-6,7-dihydro-8H-cyclopenta (g)isochroman
50 pbw amyl salicylate
50 pbw linalool
50 pbw benzyl salicylate
40 pbw rosana NB*
40 pbw citronellol
30 pbw coumarin
30 pbw cedarwood oil
30 pbw petitgrain oil
30 pbw patchouly oil
30 pbw benzyl acetate
20 pbw musk ketone
50 pbw 1,5-dimethylbicyclo [3,2,1]octan-8-yl acetate
1000 pbw

*perfume base, marketed by Naarden International N.V.

What is claimed is:

1. A carboxylic acid ester of 1,5-dimethylbicyclo[3,2,1]octan-8-ol with the formula:

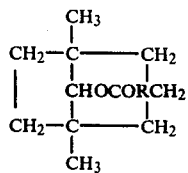

wherein R represents hydrogen, a saturated or unsaturated aliphatic or alicyclic group of 1 to 10 carbon or an aromatic hydrocarbon group of up to 7 carbon atoms, optionally substituted with an amino group.

2. The carboxylic acid ester according to claim 1, wherein R is an aliphatic or alicyclic hydrocarbon of from 1 to 7 carbon atoms selected from the class consisting of alkyl, alkenyl, alkynyl and cycloalkyl groups.

3. The carboxylic acid ester according to claim 1 wherein R is phenyl or aminophenyl.

4. The carboxylic acid ester according to claim 2 wherein R is an aliphatic hydrocarbon of from 1 to 4 carbon atoms.

5. The carboxylic acid ester according to claim 1 wherein R is hydrogen.

6. The carboxylic acid ester according to claim 1, wherein the ester grouping is selected from the class consisting of formate, acetate, propionate, butyrate, isobutyrate, pivalate, valerate and anthranitate.

7. A perfume composition containing components usual for this purpose and as a portion or all of the fragrance component, a carboxylic acid ester of 1,5-dimethylbicyclo[3,2,1]octan-8-ol with the formula:

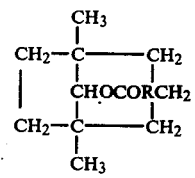

wherein R represents hydrogen, a saturated or unsaturated aliphatic or alicyclic group of 1 to 10 carbon atoms or an aromatic hydrocarbon group of up to 7 carbon atoms, optionally substituted with an amino group.

* * * * *